United States Patent
Arnott

(10) Patent No.: US 6,595,212 B1
(45) Date of Patent: Jul. 22, 2003

(54) METHOD AND APPARATUS FOR MAINTAINING AIRWAY PATENCY

(76) Inventor: Richard J. Arnott, 113 Hodil Ter., Pittsburgh, PA (US) 15238

( * ) Notice: Subject to any disclaimer, the term of this patent is extended or adjusted under 35 U.S.C. 154(b) by 0 days.

(21) Appl. No.: 09/550,986

(22) Filed: Apr. 17, 2000

(51) Int. Cl.$^7$ .............................................. A61M 16/00
(52) U.S. Cl. ............................ 128/204.23; 128/205.13
(58) Field of Search ....................... 128/204.18, 204.19, 128/204.21, 204.23, 203.28, 205.13–205.17, 200.22, 200.24, 201.27, 201.28, 205.25, 205.18, 205.24, 204.28

(56) References Cited

U.S. PATENT DOCUMENTS

| | | | | |
|---|---|---|---|---|
| 2,711,170 A | * | 6/1955 | Bornstein .............. | 128/205.13 |
| 3,216,413 A | * | 11/1965 | Mota ..................... | 128/205.13 |
| 4,340,044 A | * | 7/1982 | Levy et al. ............ | 128/204.21 |
| 4,655,213 A | | 4/1987 | Rapoport et al. | |
| 4,782,832 A | | 11/1988 | Trimble et al. | |
| 4,934,360 A | * | 6/1990 | Heilbron et al. ....... | 128/205.13 |
| 5,052,384 A | * | 10/1991 | Kaneko ................. | 128/201.27 |
| 5,065,756 A | | 11/1991 | Rapoport | |
| 5,074,297 A | | 12/1991 | Venegas | |
| 5,148,802 A | | 9/1992 | Sanders et al. | |
| 5,477,852 A | | 12/1995 | Landis et al. | |
| 5,517,983 A | * | 5/1996 | Deighan et al. ...... | 128/204.21 |
| 5,535,738 A | | 7/1996 | Estes et al. | |
| 5,572,993 A | * | 11/1996 | Kurome et al. ........ | 128/204.21 |
| 5,619,987 A | * | 4/1997 | Matsuoka .............. | 128/204.26 |
| 5,649,533 A | | 7/1997 | Oren | |
| 5,683,232 A | * | 11/1997 | Adahan ................. | 128/204.18 |
| 5,687,715 A | | 11/1997 | Landis et al. | |
| 5,937,855 A | * | 8/1999 | Zdrojkowski et al. . | 128/204.23 |
| 6,041,780 A | * | 3/2000 | Richard et al. ........ | 128/204.18 |
| 6,269,811 B1 | * | 8/2001 | Duff et al. ............. | 128/204.18 |
| 6,302,105 B1 | * | 10/2001 | Wickham et al. ...... | 128/200.27 |
| 6,349,724 B1 | * | 2/2002 | Burton et al. .......... | 128/204.18 |
| 6,357,463 B1 | * | 3/2002 | Wickham et al. ............. | 137/12 |
| 6,360,741 B2 | * | 3/2002 | Truschel ................ | 128/202.22 |
| 6,371,112 B1 | * | 4/2002 | Bibi ....................... | 128/200.24 |
| 6,401,713 B1 | * | 6/2002 | Hill et al. .............. | 128/204.18 |

* cited by examiner

*Primary Examiner*—Weilun Lo
*Assistant Examiner*—Teena Mitchell
(74) *Attorney, Agent, or Firm*—McKay & Associates, PC; Kenneth P. McKay, Esq.; George Atwell, Esq.

(57) ABSTRACT

A method is provided for effecting improved airway ventilation of a patient during sleep which involves delivering a burst or pulse of pressurized air through the patient's nose and into the patient's airway upon the termination of each breath exhalation. The apparatus of the invention includes an expandable-contractible chamber for collecting and then delivering a bolus of air through a nasal device providing sealed entry of the patient's airway, and means responsive to the exhaled breath of the patient that triggers delivery of the bolus of air, all of the foregoing preferably being contained in a compact housing that is positionable near the head of the patient.

9 Claims, 3 Drawing Sheets

FIG.6
FIG.7
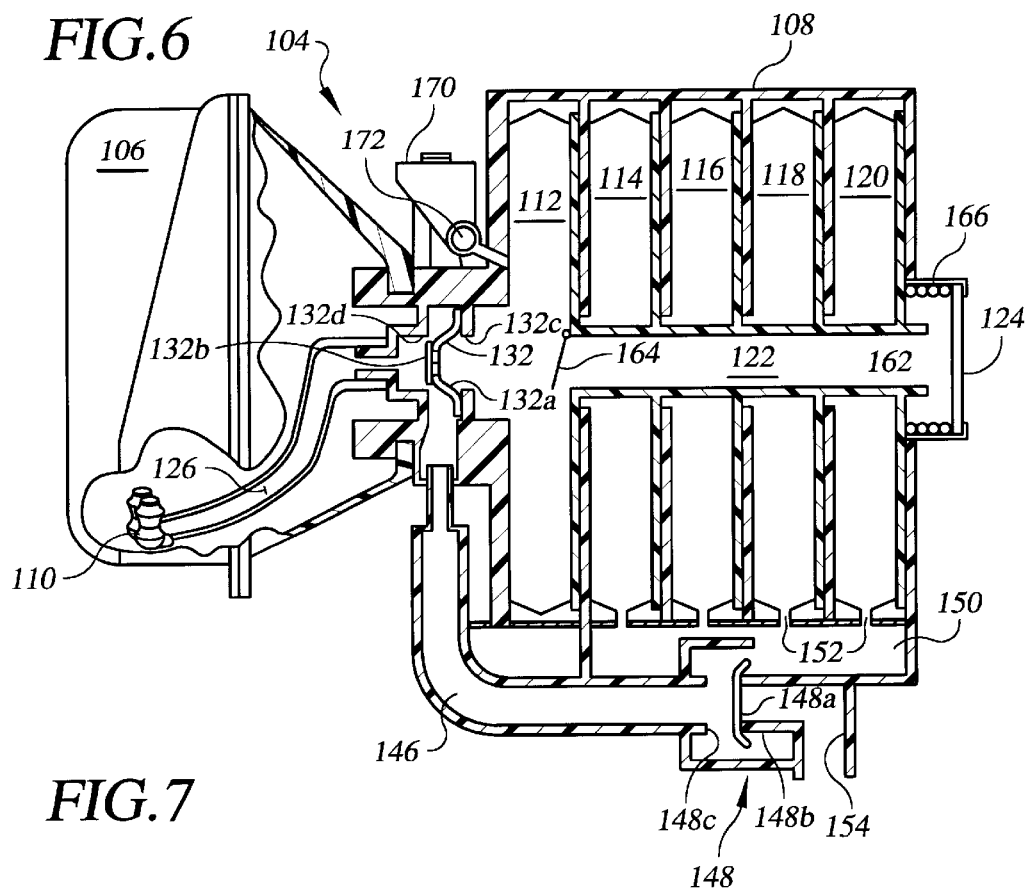
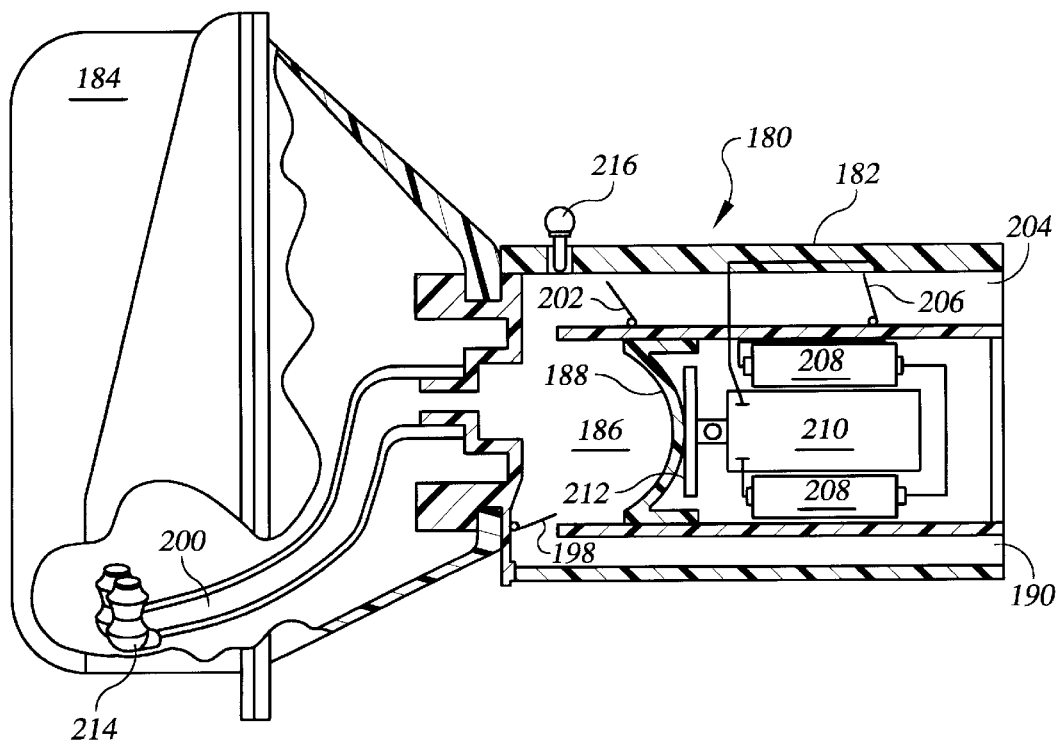

METHOD AND APPARATUS FOR MAINTAINING AIRWAY PATENCY

BACKGROUND OF THE INVENTION

Obstructive sleep apnea is a common disorder that involves tissue occlusion of the nasopharyngeal airway during sleep which impedes a patient's normal breathing cycle. Multiple sequential apnea episodes may result in severe sleep disruption of which the patient may not even be aware. Moreover, swollen tissue in the airway often results in excessive heavy snoring. Extreme sleep apnea is a serious disease which may affect as much as three percent of the adult population, and heavy snoring is much more common, particularly with overweight individuals.

Surgical intervention is always an option in alleviating obstructive sleep apnea or heavy snoring, however, most patients prefer to address the problem with non-invasive treatment. One treatment program involves the use of continuous positive airway pressure delivered to the patient's airway to maintain the airway in a continuously open state during sleep. The equipment required to deliver continuous positive airway pressure to the airway of a patient includes a fan or blower for generating a pressurized flow through a hose coupled to a mask or nasal device which the patient places over his or her nose and uses straps about the head to fasten the device in place.

Many patients cannot tolerate the application of continuous positive airway pressure, particularly because of the discomfort associated with exhalation against a continuous positive pressure. An attempt has been made to alleviate this problem by the provision of a method and apparatus which provides a substantially constant elevated airway pressure to the patient's airway, with periodic short term reductions of the elevated airway pressure to a pressure of lesser magnitude. A further advance in such treatment involves the application of alternative high- and low-level positive airway pressure wherein the low-level pressure coincides with the breath exhalation of the patient's breathing cycle.

A method and apparatus for the application of continuous positive airway pressure to a patient's airway is disclosed in U.S. Pat. No. 4,655,213, issued to Rapoport et al. The concept of providing a substantially constant elevated airway pressure with periodic short-term pressure reductions is disclosed in U.S. Pat. No. 4,773,411, issued to John B. Downs. A bi-level system of applying alternating high- and low-level positive airway pressure to a patient's airway is disclosed in U.S. Pat. No. 5,148,802, issued to Sanders et al.

The methods and apparatus disclosed in the prior art for treating patients afflicted with such maladies as sleep apnea and snoring present a number of problems which need to be addressed. The equipment utilized in such treatment is far too bulky and cumbersome. The air stream delivered to the patient tends to dehydrate the nasopharyngeal tissue. The unnatural sensation and discomfort experienced by the patient in overcoming the positive pressure during breath exhalation results in many patients abandoning the use of a system that is in all other respects quite beneficial.

SUMMARY OF THE INVENTION

The present invention comprehends the treatment of such disorders as obstructive sleep apnea or heavy snoring by providing apparatus capable of delivering a pressurized burst or pulse of air to a patient's nasopharyngeal airway at the moment of termination of the patient's breath exhalation during the breathing cycle. The pulse of pressurized airflow is sufficient to prevent the development of airway tissue occlusion and maintain the airway open for normal breathing.

Hence, it is a primary objective of the present invention to provide a method of alleviating sleep apnea or snoring by delivering ambient air to a patient's airway in the form of an air bolus, wherein the patient's exhaled air is utilized to actuate an energy storing means to cause delivery of the air bolus into the airway.

Still another objective of the present invention is to provide apparatus capable of providing a pressurized pulse of air through a nasal device and into the nasopharyngeal airway of a sleeping patient, wherein the pressurized airflow is triggered by the breath exhalation of the patient and will continue sequentially with each exhaled breath.

It is also an objective of the present invention to provide apparatus as heretofore described which preferably includes a nasal device for attachment to a patient's nose, and a housing with a chamber capable of storing a fresh air supply for release to the nasal device and into the patient's airway to thus promote a normal breathing cycle.

It is also an objective of the present invention to provide apparatus as heretofore described which is self-contained as a unitized structure that obviates the need for auxiliary remote bedside equipment requiring a large fan or compressor.

Practice of the method of this invention comprises the steps of providing a primary airflow conduit for delivering ambient air into the patient's airway and providing a bolus chamber in airflow connection with the airflow conduit which is capable of delivering a bolus of ambient air. Energy storing means responsive to the patient's breath exhalation is utilized to force the bolus of air from the chamber and through the conduit and into the patient's airway. The patient's exhaled air is used to actuate or trigger the energy storing means and cause, by the release of its energy, the delivery of the bolus of air to the patient's airway.

The invention also provides apparatus in the form of a unitary structure, such as a containment housing, with the housing being coupled to a nasal device. The nasal device may be a mask sealed to the patient's face and about the nose or a device comprising a pair of nasal delivery members, such as disclosed in U.S. Pat. No. 5,687,715, issued to Landis et al. The containment housing of the apparatus includes a first chamber for receiving breath exhaled by the patient and a second chamber for storing fresh air for delivery back to the patient at a predetermined time during the patient's breathing cycle. The chambers are expandable and operatively interconnected whereby expansion of the first chamber causes expansion of the second chamber. An energy storing means is provided within the containment housing which is adapted to operate, at the moment of completion of the patient's breath exhalation, to contract both of the expandable chambers and cause a momentary burst of pressurized airflow to be ejected from the second chamber and through the nasal device to the patient's airway. The pressurized airflow is only momentary, whereby completion of air inhalation occurs naturally and voluntarily by the patient.

Details of the method of the present invention and the elements and structural characteristics of several embodiments of the apparatus will become apparent from the ensuing detailed description when considered in reference to the accompanying drawings.

BRIEF DESCRIPTION OF THE DRAWINGS

FIG. 6 is an elevational view in vertical section of apparatus which incorporates the structural and operative characteristics first disclosed in FIGS. 1–5;

FIG. 7 is an elevational view in partial vertical section illustrating an alternative embodiment of apparatus of the present invention;

DETAILED DESCRIPTION OF THE PREFERRED EMBODIMENTS

Figure 1:
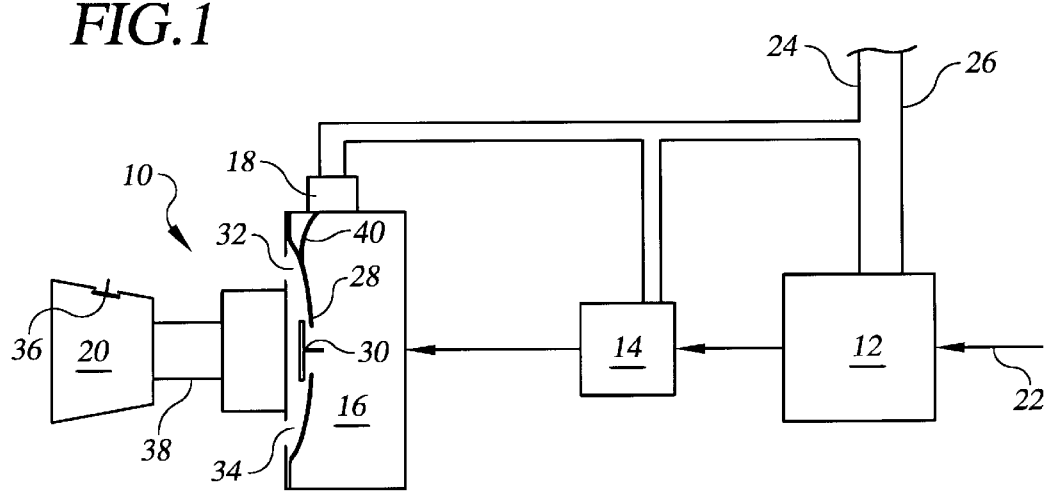
FIG. 1 is a schematic representation which illustrates both the method and basic apparatus for practicing the present invention.

FIG. 1 schematically illustrates an assembly 10 including an airflow generator 12, an electromagnetic solenoid 14, a dual valve assembly 16, a normally-open electrical switch 18, and a mask 20. The airflow generator 12 may be a blower or fan of the type used to produce a pressurized airflow. The solid line arrows mark the air stream flow path, beginning with ambient air drawn into the airflow generator as indicated by arrow 22. The electric current to operate the flow generator is supplied through conductors 24 and 26, which also supply current to solenoid 14 through switch 18. The airflow generator 12 is intended to operate continuously whereby a constant head of pressurized air is maintained to the solenoid 14. However, the solenoid 14 is normally closed and will permit air passage therethrough to the dual valve assembly 16 only when the solenoid 14 is caused to open by switch 18.

The dual valve assembly 16 of FIG. 1 includes a flexible circular diaphragm 28 and a disc valve 30 mounted on the diaphragm 28. In its relaxed position (not shown), the diaphragm 28 will cover and seal apertures, such as aperture 32 and aperture 34. The disc valve 30 is a circular flexible thin rubber membrane which normally seals against the inside surface of the diaphragm 28 but will flex open in response to pressurized airflow from the solenoid 14 and allow the airflow to pass through the valve arrangement and thence into mask 20.

It should be noted that the mask 20 is provided with a normally-closed disc valve 36 which will respond to inhalation by the patient and open to permit entry of ambient air. The mask 20 is meant to be worn in sealed relation to the nose of a patient whereby ambient air during inhalation will pass into the mask past valve 36. Exhaled breath will cause valve 36 to close whereby the breath flow will be in the direction of the dotted line arrow 38 and into the dual valve assembly 16. Breath pressure entering the dual valve assembly 16 causes the disc 30 to seal against the diaphragm 28 and stretches the diaphragm from a sealing linear disposition (not shown) to the position shown in FIG. 1. A spring-biased switch trigger or toggle 40 extending from switch 18 is contacted by the outwardly-flexed diaphragm 28 whereby the toggle 40 is pivoted from left to right as shown in FIG. 1. This pivoting action of the toggle 40 sets the switch internally whereby, as the diaphragm 28 relaxes, the toggle 40 will pivot back to its original position and, at the same, close internal contacts of the toggle 40 to complete the electrical circuit to the solenoid 14. The solenoid 14 is thereby caused to cycle open and then immediately reclose after having permitted a burst of pressurized air to move into the dual valve assembly 16 and past the disc valve 30 and into the mask 20. The pressurized airflow burst is directed into the nasopharyngeal airway of the patient as the patient's inhalation action occurs, and ambient air moves through valve 36 to allow the patient to complete the breath intake voluntarily. The subsequent exhalation by the patient repeats the described process whereby a pulse or burst of pressurized air is delivered to the mask 20 and thence to the patient's airway as a function of each breathing cycle.

Although FIG. 1 broadly illustrates the underlying method of the present invention, it is preferred that the apparatus for practicing the method be contained in a compact housing positioned adjacent the head of the patient and that it is not dependent upon a continuously operating bedside blower or household electrical connection for its energy source. Presently preferred embodiments of the invention involve utilization of dual chambers contained in a compact housing, as illustrated and explained hereinafter with reference to FIGS. 2–8.

Figure 2:
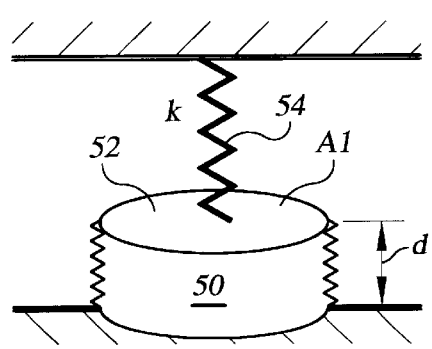
FIGS. 2 and 3 are schematic representations which illustrate the physical principles underlying the method and basic operation of the apparatus of the present invention.
Figure 3:
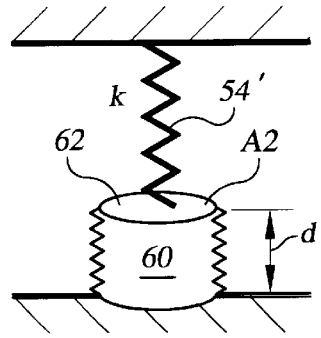

FIGS. 2 and 3 demonstrate the physical principles underlying the mechanical operation of the several embodiments set forth and hereafter discussed in reference to FIGS. 4–8. FIG. 2 shows a pneumatically expandable-contractible exhalation chamber 50 that becomes inflated by the exhaled air from a patient at a certain pressure above atmospheric pressure so that a top plate 52 of the chamber 50, having an area Al, is raised against a compressible elastic element 54. The elastic element 54 may be a compression spring having a constant K. The total vertical force exerted against the elastic element 54 is the product exhaled air pressure multiplied by the top plate area Al. The elastic element 54 is compressed until its downward force equals the upward force of the top plate 52. An equilibrium position is obtained when the total upward force equals the spring constant multiplied by a distance d, where d is the distance of movement measuring the shortening of the elastic element 54.

FIG. 3 shows a pneumatically expandable-contractible bolus chamber 60 that works against an elastic element $54^1$. The force in the compressed elastic element $54^1$ is then applied to the bolus chamber 60 that is already filled with fresh air at atmospheric pressure when the exhaled breath is released from chamber 50. The elastic element $54^1$ exerts a downward force on a top plate 62 of the chamber 60. The top plate 62 has an area A2, where A1 (FIG. 2) is greater than A2. The air contained in the chamber 60 is under a positive initial pressure which is available to create a momentary airflow or bolus capable of relieving an apneic obstruction in a patient's airway. Valve and linkage means (not shown) operatively-connected between chamber 50 and chamber 60 would be utilized to mechanically translate the expanding action of chamber 50 to cause chamber 60 to simultaneously expand and draw in ambient air, and to allow both chambers to simultaneously expand and draw in ambient air, and to allow both chambers to simultaneously contract when the momentary positive airflow (bolus) has been ejected from chamber 60.

Figure 4:
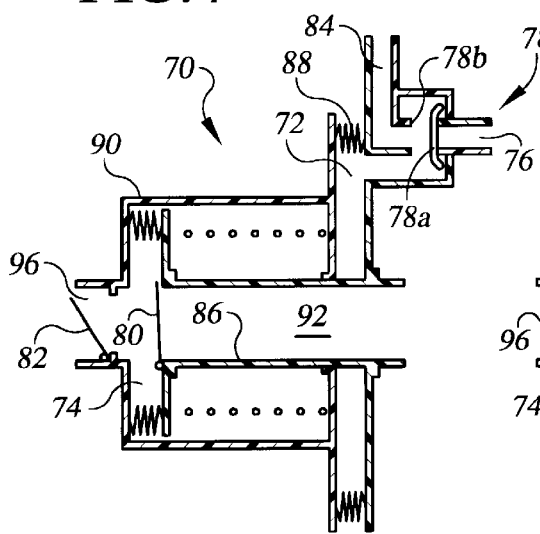
FIGS. 4 and 5 are elevational views in vertical section of a bench-test embodiment of apparatus of the present invention.
Figure 5:
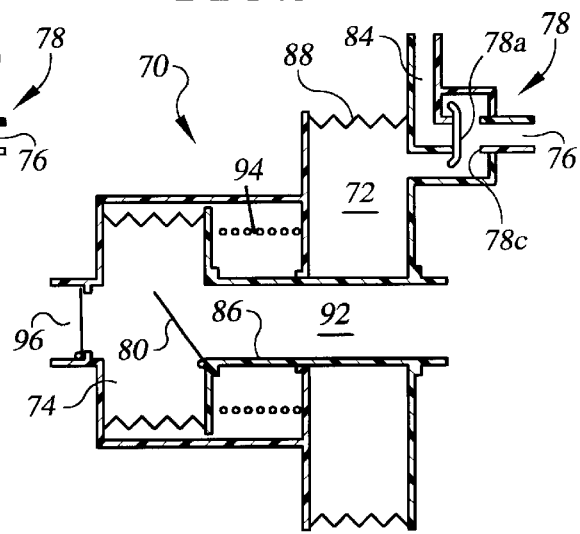

FIGS. 4 and 5 illustrate bench model apparatus for practicing and demonstrating the method of the present invention. FIG. 4 shows a structure or apparatus 70 defining an exhalation chamber 72 and a bolus chamber 74. In the use of the apparatus exhaled breath from the patient enters the exhalation chamber 72 through an entry port 76. Inboard from the entry port 76 is a circular semi-flexible silicon disc 78a which coacts with spaced-apart valve seats 78b and 78c. The disc 78a is movable between a first position, as shown in FIG. 4, to a second position, as shown in FIG. 5, and is responsive to low pressure airflow to change its position. Air enters chamber 72 through entry port 76, causing the disc 78a to close off an outlet passage 84 whereby all entering air will flow to the chamber 72. Sidewall structure serves as linkage 86 between the chambers. The expansion of chamber 72 in response to airflow directed thereto through the entry port 76 causes the linkage 86 to shift to the left as shown in FIG. 4 also undergoes expansion. Both of the chambers 72 and 74 have pleated accordion-like exterior sidewalls 88 and 90 which facilitate expansion of the chambers. As chamber 74 expands from the disposition shown in FIG. 4 to that which is shown in FIG. 5, and in response to the expansion of chamber 72, motion of linkage 86 causes chamber 74 to expand and draw air in through a central passage 92. The airflow through passage 92 moves past open flapper valve 80 and into the chamber 74. The initial negative pressure in chamber 74 as it begins to expand causes a valve 82 to close and valve 80 to open whereby the chamber 74 takes in ambient air through the passage 92. The expansion of the chambers 72 and 74 and the movement of linkage 86 causes a compression spring 94 to compress from its expanded disposition shown in FIG. 4 to a contracted position as shown in FIG. 5. When both chambers 72 and 74 have fully expanded and the exhalation has ended, the force of energy in the spring 94 causes the linkage 86 to shift back from the disposition shown in FIG. 5 to that which is shown in FIG. 4 whereby the volume of air in each chamber is pressurized to create simultaneous discharge airflows. Specifically, the lack of pressure from exhalation and contraction of chamber 72 causes the valve disc 78a to close off the port 76 whereby air from the chamber 72 will be discharged through the outlet 84. Simultaneously, contraction of the chamber 74 causes valve 80 to close and valve 82 to open and eject pressurized air though passage or discharge port 96. The bolus of air forced out of chamber 74 past valve 82 constitutes air available for delivery to a patient's airway.

FIG. 6 illustrates apparatus in accordance with the present invention which operates pursuant to the principles explained in reference to FIGS. 2–5. The apparatus 104 shown in FIG. 6 comprises a mask 106 and a housing 108. The housing 108 is rigidly attached to the mask assembly whereby the mask 106, once strapped in operative position against the face of a patient, serves as a housing support. In the embodiment of the invention illustrated in FIG. 6, it is not particularly important that the mask seals against the patient's face because a nasal device 110 is utilized for airflow communication attachment to the patient's nares as hereafter explained in greater detail. Within the housing 108 is a bolus chamber 112 and an exhalation chamber comprised of four compartments 114, 116, 118, and 120. The housing 108 has a central air passage 122 adapted to take in ambient air through a filter 124. The air passage 122 constitutes a conduit extending from the filter 124 and centrally through the housing 108 and into the bolus chamber 112. The apparatus 104 as heretofore described presents a means of practicing the method of the invention in a unitary compact form that is relatively simple in its operational concept. With the mask 106 disposed against the face and about the nose of the patient, air is inhaled centrally through the housing passage 122. Valve structure 132 opens during inhalation whereby the air moves from the passage 122 and across the bolus chamber 112 and thence past the valve structure 132 and through a conduit 126 to the patient's airway. The valve structure 132 constitutes a stretchable diaphragm 132a, a flexible valve disc 132b carried on the diaphragm, and opposed valve seats 132c and 132d. The valve 132 is a dual valve structure which normally seals against the valve seat 132c to prevent passage of air from passage 122 to and into conduit 126. The valve structure is a diaphragm 132a that supports a flexible disc 132b that normally seals against an opening in the center of the diaphragm 132a. The valve 132 allows airflow in one direction only by the peripheral flexure of the disc 132b away from the diaphragm 132a, and the diaphragm 132a is capable of stretching or rolling, in response to airflow from passage 122, to seal off airflow to a passage 146. Inhalation by the patient through the nose connection 110 establishes an ambient airflow into the filter 124, across the passage 122, and through the valve 164 and 132 to the conduit 126. Upon exhalation, airflow from the airway of the patient is delivered through conduit 126 and downwardly into passage 146, with the valve 132 preventing any airflow into bolus chamber 112. The exhaled air stream from the patient moves through the passage 146 and into valve structure 148 and thence into a manifold or distribution chamber 150. The pressurized airflow from the manifold 150 is distributed through openings 152 into compartments 114–120, which constitute the exhalation chamber.

The resultant build-up of air pressure within the compartments 114–120 of the exhalation chamber causes a shift in the internally-disposed rigid linkage 162. The linkage 162 is adapted to shift from a chamber-empty position (not shown) and to the right, as viewed in FIG. 6, to a chamber-filled position. As the exhalation chamber takes in air and expands, ambient airflow causes valve 164 to open to allow the ambient air to fill bolus chamber 112. Termination of the patient's exhaled breath results in a slight back pressure in the manifold 150, causing the disc 148a to shift from its sealed position against valve seat 148b to a second sealed position against valve seat 148c. An energy storing means, in the form of compression spring 166, acts to push the rigid linkage 162 from right to left as viewed in FIG. 6, thereby causing contraction of the exhalation chamber and the bolus chamber 112.

This results in the air within the exhalation chamber (compartments 114–120) to be expelled through outlet port 154. Air pressure within the bolus chamber 112 causes valve 164 to close whereby the bolus of air is forced against the diaphragm 132 such that disc 132b will peripherally flex to allow the bolus to proceed into conduit 126 and thence through the nasal connection 110 and into the patient's airway. The ambient air previously captured in the bolus chamber 112 is forced as a pulse or thrust into the patient's airway just as the patient is starting to inhale. The bolus of air delivered to the patient's airway is sufficient to cause the inhalation to begin. The apneic obstruction in the airway is caused to relax whereby the patient finishes the breath inhalation as part of the natural breathing cycle.

Also illustrated in FIG. 6 is a reservoir 170 into which medication in liquid form may be stored and allowed to disperse into the bolus chamber 112, the rate of dispersal being controlled by a metering device 172. Many patients who are afflicted with sleep apnea also suffer asthmatic symptoms, including swelling of mucous membranes and bronchial tube spasms manifested by shortness of breath, whereby gasping causes the individual to awaken. The administration of medication into the air stream and thence into the bronchial tubes during inhalation is now common and can be quite effective in promoting natural sleep. The provision of the reservoir 170 for this purpose, whereby droplets of medication can be metered into the bolus of air in the chamber 112, is an elective option that can be made available to the user of the device illustrated in FIG. 6.

FIG. 7 illustrates an alternate embodiment of the apparatus of the present invention comprising a unified structure 180. The structure 180 includes a housing 182 coupled to a mask 184. Within the housing 182 is a bolus chamber 186 partially defined by a flexible diaphragm 188. A nasal device 214 constitutes a means for attaching the apparatus in flow communication with a patient's airway. The function of apparatus 180 begins immediately upon it being placed in its operative position, with the nasal device 214 inserted into the patient's nares. As the patient inhales, ambient air enters through inlet 190 and moves through passage 194 and thence into the chamber 186. Flapper valve 198 pivots to an open position during inhalation. Inhalation continues by passage of air through the conduit 200 and into the patient's airway. Exhaled breath passes out through the conduit 200 and into the chamber 186. A slight pressure is sufficient to close valve 198 whereby the exhaled breath progresses past open valve 202 and outwardly through passage 204. A pressure-sensitive electrical switch 206 is caused to close its contacts by the exhaled breath moving thereagainst, completing a circuit to an energy storing means in the form of batteries 208 that actuate a solenoid 210. Closure of the switch 206 is only momentary and sufficient to energize the solenoid 210 whereby its plunger 212 acts against the diaphragm 188, causing the diaphragm to flex from right to left as shown in FIG. 7, and then return to its start position. The resulting increased air pressure within the chamber 186 is forced through the conduit 200 and into the patient's airway. Means, in the form of a thumb screw 216 threaded into an accommodating aperture in the housing 182, may be utilized to regulate the intensity of the air pressure bolus within the chamber 186 by allowing minimal controlled leakage.

Figure 8:
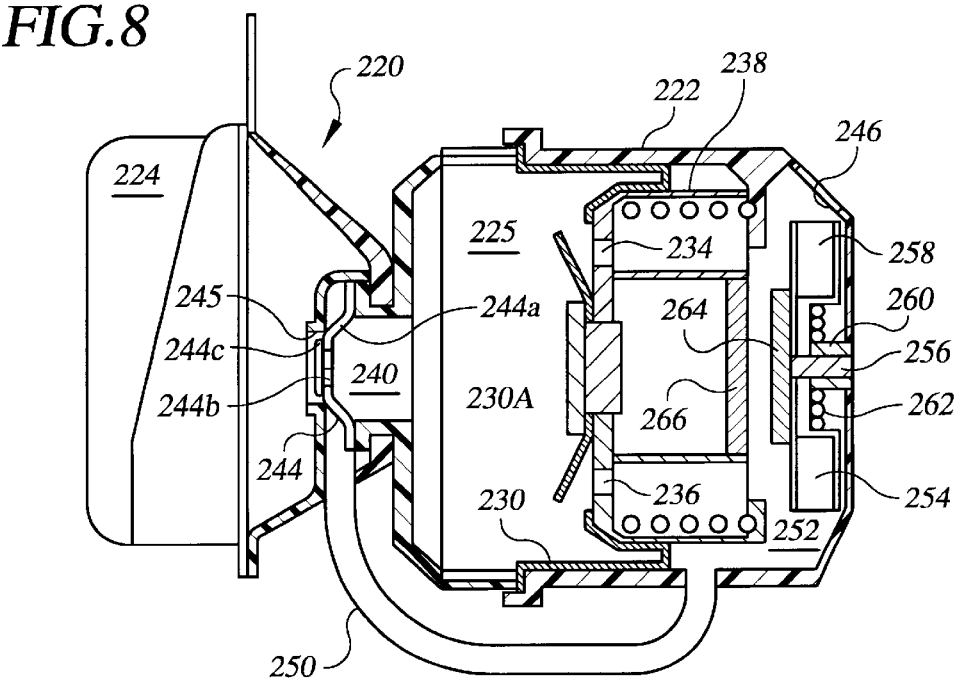
FIG. 8 is an elevational view in vertical section illustrating still another alternative form for the apparatus of the present invention.

FIG. 8 illustrates apparatus 220 which utilizes the interaction of permanent magnets to cause delivery of a bolus of air to the patient's airway. The apparatus 220 comprises a housing 222 and a mask 224. The mask 224 must, in this embodiment, be of the type that seals tightly about the nose of the patient whereby breathing occurs entirely through the apparatus. Within the housing 222 is a bolus chamber 225 partially defined by a flexible rolling diaphragm 230. Centrally located on the diaphragm 230 is a flexible disc valve 230A which normally blocks apertures 234 and 236 provided in the face of a piston 238. The only outlet from the chamber 225 is a passage 240 normally closed by a valve structure 244. The valve structure 244 comprises a flexible diaphragm 244a with openings 244b therethrough and a centrally-attached flexible disc 244c. The piston 238 is mounted to be reciprocal within the housing 222 from a retracted position, as shown in FIG. 8, to a fully extended position which would be to the left.

To facilitate its operation, the apparatus 220 is positioned: usually strapped in place, against a patient's face whereby the nose is within the mask 224. Ambient air is inhaled by the patient through an opening 246. The inhaled airflow is drawn through the hollow body of the piston 238 and through the openings 234 and 236. Disc valve 230a is caused to flex open by the pressure of the inhaled air stream whereby air passes through chamber 225 and thence through openings 244b in the valve structure 244. Disc valve 244c is flexed open by the positive pressure of the inhaled air stream. Upon completion of inhalation, the patient exhales, causing the valve structure 244 to close whereby the exhaled breath is channeled through a conduit 250 and thence into a rearward chamber 252 in the housing 222. Within the chamber 252, the exhaled air stream strikes against a rotatable impeller 254 having an axle 256 and radially outwardly-extending blades 258. The hub 260 of the impeller 254 has a recessed area containing a coil spring 262. Attached to the impeller 254 is a split disc-shaped permanent magnet 264. Spaced from the magnet 264 and attached to the piston 238 is another permanent magnet 266. The magnets 264 and 266 are preferably rare earth Neodymium discs, one of which is firmly attached to the hub 260 of the impeller 254, and the other being firmly affixed to the back side of the piston 238. Such magnets, made from a Neodymium iron-boron material, have seven to ten times more holding or repulsion force than other magnetic materials. The magnets are magnetically charged to repulse each other whereby, when magnet 264 is rotated on its axis 180° the repulsive force causes the magnet 266 to move from right to left as viewed in FIG. 8, thereby causing the piston 238 to move from its first or starting position to its second or extended position such that diaphragm 230 is deformably distended in the direction of the mask 224.

As shown in FIG. 8, the magnets 264 and 266 are in an equilibrium position, however, when exhaled air from the patient moves through conduit 250 and thence through the rearward chamber 252, the air pressure against the impeller blades 258 cause the impeller 254 to rotate 180° until the air stream escapes through housing opening 246. The rotation of the impeller 254 rotates the split magnet 264 relative to the split magnet 266 whereby a magnetic repulsive force acting between the magnets causes the piston to move away from the magnet 264. A light-duty return spring 262 disposed about the shaft and bearings of the impeller 254 returns the impeller 254 to its starting position whereby the repulsive force between the magnets is neutralized. When the piston 238 is driven from its first position to its second position within the housing 222, the bolus of air contained within the chamber 224 is driven against and past the valve structure 244 and thence to the airway of the patient. The apparatus 220 serves to provide a bolus of air into the patient's airway at the termination of each exhalation by the patient during the patient's breathing cycle and, in each sequential cycle, the patient completes inhalation naturally and without assistance before the next exhalation occurs.

Figure 9:
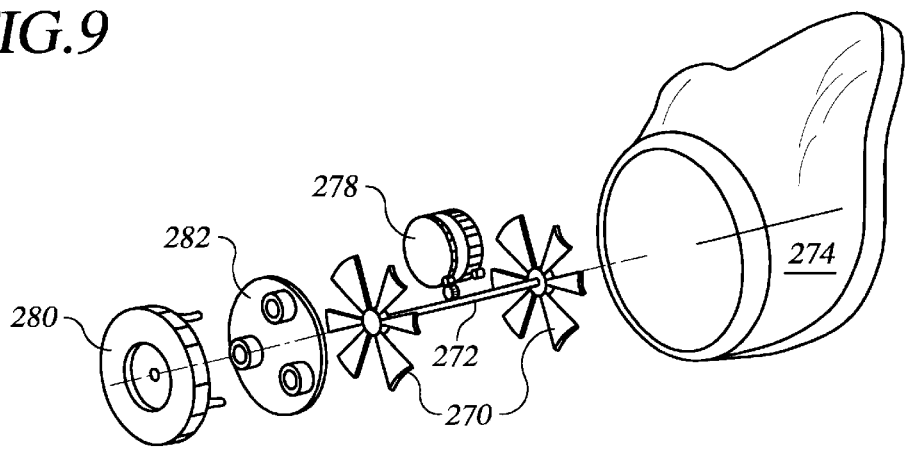
FIG. 9 is a perspective view of certain components intended for use in still another embodiment of the present invention.

In view of the description of the operation of the various embodiments of the present invention heretofore presented, it should be apparent to those skilled in the art that the method of the invention may be practiced by the provision of a mechanical variation such as shown in FIG. 9. FIG. 9 illustrates a pair of vanes 270 rotatably mounted on an axis 272. The vanes 270 can be driven to rotate by exhaled breath coming from a mask 274 to thereby rotate the shaft or axis 272 and correspondingly wind an energy-storing device 278. At the completion of each exhalation by the patient, a wound spring within the energy-storing device 278 will then cause the shaft 272 to counter-rotate whereby an impeller 280 and planetary gears 282 will force a pressurized airflow back into the mask and thence into the airway of the patient. The aforedescribed function occurs as an incident of each breathing cycle of the patient.

Figure 10:
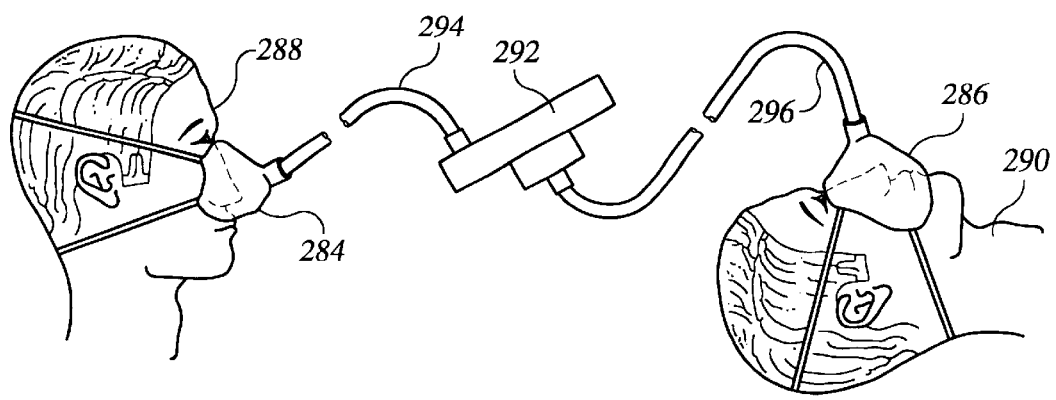
FIG. 10 illustrates a novel or ancillary use contemplated for the invention.

A further use of the invention is contemplated as shown in FIG. 10 which would include first and second masks 284 and 286 by which a first person 288 could provide hands-free ventilation to a second distressed person 290. For this embodiment, momentary positive air pressure would be provided to the first mask 284, an exhalation chamber, and a collection or bolus chamber (not shown) as illustrated in accordance with the invention embodiments herein previously described. The exhalation chamber would receive the exhaled breath of the first assisting person 288, and the bolus chamber would be adapted to deliver fresh ambient air to the second distressed person 290. With the device 292 coupled intermediate to the first and second persons, by means of hoses 294 and 296, a pressurized flow of ambient air could be delivered from the assisting person 288 to the distressed person 290 as a resuscitation measure.

While various embodiments of the present invention have been disclosed and described herein, it should be understood that the preferred version of the apparatus is compact, portable, and comparatively inexpensive as compared to prior art devices that utilize large blowers or compressors to achieve a similar function by continuous or bi-level airflow provision. It should be further understood that while the invention has been disclosed and described with reference to specific alternative embodiments, there are variations and modifications which may be introduced that will nevertheless come within the scope and spirit of the invention as defined by the appended claims.

I claim:

1. A method of relieving a patient of obstructive sleep apnea, comprising the steps of:

providing a means of directing exhaled breath from an airway of said patient to a first expandable chamber;

providing a second expandable chamber for collecting ambient air, wherein said second expandable chamber is operatively connected to said first expandable chamber by a linkage;

providing an energy storing means further connected to said linkage, wherein said energy storing means actively operates to store energy as a function of said first expandable chamber being expanded by said exhaled breath of said patient and movement of said linkage; and utilizing energy from said energy storing means to contract said second expandable chamber and force air from said second expandable chamber and into said airway of said patient.

2. Apparatus for assisting breathing of a patient during sleep, comprising:

a containment housing for positioning adjacent to a head of said patient;

a bolus chamber within said containment housing for storing a bolus of air;

an exhalation chamber within said containment housing connected to said bolus chamber by a rigid linkage;

an energy storing means operatively linked to said rigid linkage and within said containment housing for forcibly displacing said bolus of air.

3. The apparatus of claim 2, further comprising an entry port through which an exhaled breath from said patient may enter said exhalation chamber.

4. The apparatus of claim 3, further comprising a semi-flexible silicon disc inboard from said entry port adapted to coact with spaced apart valve seats.

5. Apparatus for assisting breathing of a patient during sleep, comprising:

a containment housing enclosing an exhalation chamber and a bolus chamber, both of which are expandable and contractible;

linkage means connectively linked between said exhalation chamber and said bolus chamber to expand and contract as a function of said expansion and said contraction of said exhalation chamber;

biasing means operatively connected to said linkage means to urge said linkage means to contract both said exhalation chamber and said bolus chamber;

said exhalation chamber having airflow communication means for conducting exhaled breath thereto from an airway of said patient whereby said exhalation chamber expands; and said bolus chamber being adapted to receivably store fresh ambient air and having airflow communication means for directing a thrust of air therefrom and into said airway of said patient as both said exhalation chamber and said bolus chamber contract.

6. Apparatus for therapeutic respiratory control of a patient, including, in combination:

a mask for fitted placement against a face and over a nose of said patient;

a containment housing coupled in airflow communication to said mask;

an electrical energy source;

an airflow generating means within said containment housing capable of intermittently generating a pressurized airflow into said mask and in response to energy directed thereto from said electrical energy source; wherein said airflow generating means comprises a flexible diaphragm;

normally-open switch means disposed to close as a function of said patient exhaling breath from said mask; and, a solenoid disposed within said containment housing to allow a plunger to flex said flexible diaphragm and thereby generate said pressurized airflow into said mask.

7. The apparatus of claim 6, further comprising a thumb screw threaded into an accommodating aperture in said containment housing for airflow intensity regulation.

8. Apparatus for therapeutic treatment of a patient susceptible to obstructive sleep apnea, comprising:

a nasal device for attachment to said patient for inhalation and exhalation therethrough, and a housing enclosing:

a first expandable-contractible chamber for supplying momentary pressurized air to couplers, through a nose of said patient, and into a nasopharyngeal airway of said patient;

a second expandable-contractible chamber adapted to expand in response to an exhalation of said patient;

both said first expandable-contractible chamber and said second expandable-contractible chamber being linked by a linkage whereby expansion of said first expandable-contractible chamber causes expansion of said second expandable-contractible chamber;

an elastic element responsive to store energy as a function of said expansion; and, a medication retention reservoir in fluid communication with said first expandable-contractible chamber.

9. The apparatus of claim 8, wherein said medication retention reservoir further comprises a metering device for monitoring a rate of dispersal of medication.

* * * * *